United States Patent [19]

Simon et al.

[11] Patent Number: 4,582,698

[45] Date of Patent: Apr. 15, 1986

[54] PROCESS FOR IMAGING CARDIAC INFARCTS

[75] Inventors: Jaime Simon, Angleton; David A. Wilson, Richwood, both of Tex.; Wynn A. Volkert, Columbia, Mo.

[73] Assignee: The Dow Chemical Company, Midland, Mich.

[21] Appl. No.: 533,332

[22] Filed: Sep. 19, 1983

[51] Int. Cl.$^4$ .................... A61K 43/00; A61K 49/00
[52] U.S. Cl. ............................ 424/1.1; 260/502.5 E; 424/9; 562/499
[58] Field of Search .................. 424/1.1, 9; 260/429.5, 260/429.2, 429.7, 502.5 E; 562/499

[56] References Cited

U.S. PATENT DOCUMENTS

| | | | |
|---|---|---|---|
| 3,983,227 | 9/1976 | Tofe et al. | 424/1.1 |
| 4,036,945 | 7/1977 | Haber | 424/1.1 |
| 4,234,562 | 11/1980 | Tofe et al. | 424/1.1 |
| 4,385,046 | 5/1983 | Milbrath et al. | 424/1.1 |
| 4,387,087 | 6/1983 | Deutsch et al. | 424/1.1 |

FOREIGN PATENT DOCUMENTS

| | | | |
|---|---|---|---|
| 1518118 | 12/1973 | Fed. Rep. of Germany | 424/1.1 |
| 1081124 | 6/1965 | United Kingdom | 424/9 |

OTHER PUBLICATIONS

"Heart Imaging with Cationic Complexes of Technetium", Science, 214, 85–86 (1981).
"Infarct Sizing in Awake, Unsedated Dogs with Acute Anterior Myocardial Infarcts", Journal of Nuclear Medicine, 17, (6), 534 (1976).
"Uptake of Tc–99m Pyrophosphate (PYP) and Calcium (Ca) in Irreversibly Damaged Myocardium", Ibid.
"Uptake of Six Techneitum–99m Radiopharmaceuticals and Strontium–85 in Vasopressin–Induced Rabbit Myocardial Infarction", Ibid, 534–535.
"A New Method for Radionuclide Imaging of Myocardial Infarcts", Radiology, 110, 473 (1974).
"Radiopharmaceuticals in Cardiovascular Nuclear Medicine", Seminars in Nuclear Medicine, vol. IX, No. 4, 241–256 (1979).
"Tc–99m HMDP (Hydroxymethylene Diphosphonate): A Radiopharmaceutical for Skeletal and Acute Myocardial Infarct Imaging", Journal of Nuclear Medicine, vol. 21, No. 10, 961–966 (1980).

Primary Examiner—Christine M. Nucker
Attorney, Agent, or Firm—A. C. Ancona

[57] ABSTRACT

The imaging of cardiac infarcts with complexed radioactive metals is improved by employing as the complexing agent a compound of the formula

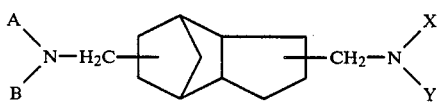

wherein substituents A, B, X and Y are each independently selected from radicals including hydrogen, hydroxyalkyl (wherein the alkyl group contains 2–6 carbon atoms), methylenephosphonic, methylene-, ethylene-, and propylenesulfonic, carboxylic acid radicals (having 2–4 carbon atoms) and the alkali or alkaline earth metal, ammonia and amine salts thereof and wherein at least one A, B, X and Y is methylenephosphonic acid or a salt thereof. In particular Tc-99m complexes have been found useful for imaging damaged cardiac tissue.

4 Claims, No Drawings

PROCESS FOR IMAGING CARDIAC INFARCTS

BACKGROUND OF THE INVENTION

Radiopharmaceuticals are widely used to evaluate cardiac function. Among the radioactive agents employed are, for example, $^{99m}$Tc-labeled human serum albumin and $^{99m}$Tc-labeled red blood cells for determination of cardiac blood volume, left ventrical wall motions and, ejection fractions. Evaluation of coronary blood flow can be done with radioactive inert gases, such as Xenon-133 and Krypton-85, or with radioactive labeled particles, e.g. $^{99m}$Tc-macroaggregated albumin.

Radionuclides that are often considered analogues of potassium have been used for myocardial perfusion studies. Of these, $^{201}$Tl+ is presently the agent of choice. The mechanism of thallium uptake may be via the Na-K ATP-ase pump. Myocardial infarctions or reduced coronary blood flow will cause a decrease in the uptake of K+ or $^{201}$Tl+ in underperfused cardiac muscle. Infarcts or ischemic myocardium will be visualized as areas of low $^{201}$Tl+ activity. This type of study is called "cold spot" imaging. "Cold spot" imaging can also be done using labeled fatty acids, e.g. $^{11}$C-palmitate and $^{123}$I-fatty acids, and recent work indicates lipophilic cationic $^{99m}$Tc complexes may be used.*

*Science, 214, 85 (1981)

Several agents have been shown to localize in infarcted myocardial tissue. Because the activity is concentrated in the damaged portions of the heart, this type of study is called "hot spot" imaging. These agents have proven to be more sensitive than "cold spot" imaging for the detection of myocardial infarcts.

Many non-technetium agents have been proposed for "hot spot" cardiac imaging. Thus, $^{131}$I-Rose Bengal, $^{203}$Hg-chlormerodrin, $^{67}$Ga-citrate, and $^{203}$Hg-diiodomercurihydroxyfluorascein have been suggested. However, these are generally not used because of the popularity of Tc-99m-agents.

Many organ scanning agents have been replaced with complexes of Technetium-99m. This nuclide has ideal physical properties ($T_{\frac{1}{2}}=6$ hour, gamma photon of 141 kev) for imaging. In addition, it is readily available because of the Mo-99/Tc-99m generators. Thus, the majority of imaging is now done using Tc-99m.

Technetium-99m is obtained from generators in the +7 oxidation state as the pertechnetate ion (TcO$_4^-$). In order to form a complex, Tc must be reduced to a lower oxidation state, i.e. +3, +4 or +5. Although other reducing agents can be used, Sn$^{2+}$ has been employed most often. Thus, Tc-99m complexes can be formed by reduction of TcO$_4^-$ using Sn$^{2+}$ in the presence of a complexing agent. This is usually done in an aqueous saline solution that is suitable for intravenous injection.

Commercial complexing agents are sold as "radiopharmaceutical kits." A "kit" consists of an evacuated vial containing the complexing agent, a reducing agent, and possibly a buffer and stabilizers. To prepare the Tc-99m complexes, a few milliliters of sodium pertechnetate solution in saline is injected into the vial. The resultant solution is used for imaging.

Various $^{99m}$Tc-chelates have been shown to accumulate in infarcts.* Thus, $^{99m}$Tc-hydroxyethylenediphosphonate, $^{99m}$Tc-methylenediphosphonate, $^{99m}$Tc-glucoheptonate have been tested, some of which also show high bone uptake.

*J. Nuclear Med., 17, 534 (1976)

The most widely used agent for "hot spot" cardiac imaging is $^{99m}$Tc-pyrophosphate. Although many of the $^{99m}$Tc-phosphates and phosphonates have an infarct to normal myocardium ratio comparable to $^{99m}$Tc-pyrophosphate, the latter is preferred because of its relatively high infarct to bone ratio when compared to other $^{99m}$Tc bone seeking agents and thus, there is less interference from the ribs and sternum.*

**Radiology, 110, 473 (1974)
***Seminars in Nuclear Medicine, Vol. IX, No. 4, 241 (1979)

Although $^{99m}$Tc-pyrophosphate is the agent of choice to image acute myocardial infarcts, it still presents problems. For example, interference due to uptake in overlying skeletal structures, the inability to detect recent infarcts and the relatively slow blood clearance limit the utility of $^{99m}$Tc-pyrophosphate. Therefore, a need still exists for new improved agents to image cardiac infarcts.

Certain new stable organic complexing agents for Tc-99m which are methylenephosphonic acid derivatives of dicyclopentadienebis(methylamine) have been disclosed as improved skeletal imaging agents. These are disclosed in our patent application U.S. Ser. No. 505,665 filed June 20, 1983, entitled "Radioactive Metals Complexed with Phosphonate Derivatives of Dicyclopentadienebis(methylamine)".

The same complexes have now been determined to be excellent radio imaging agents for damaged cardiac tissue.

SUMMARY OF THE INVENTION

Improved imaging of cardiac infarcts has been discovered when using as a complex for Tc-99m a compound of the formula

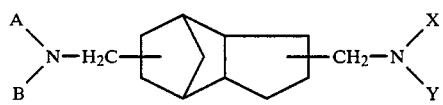

wherein substituents A, B, X and Y are each independently selected from radicals including hydrogen, hydroxyalkyl (wherein the alkyl group contains 2-6 carbon atoms), methylenephosphonic, methylene-, ethylene-, and propylenesulfonic, carboxylic acid radicals (having 2-4 carbon atoms) and the alkali or alkaline earth metal, ammonia and amine salts thereof and wherein at least one A, B, X and Y is methylenephosphonic acid or a salt thereof.

DETAILED DESCRIPTION OF THE INVENTION

The invention concerns the use of novel complexes for imaging myocardial infarcts. The complexing agents were found to form stable Tc-99m complexes when Sn$^{2+}$ was added to a saline solution containing the complexing agent. The complexes clear readily through the kidneys with skeletal uptake. Minimal uptake is present in other organs (e.g. liver). Large amounts of the complexes are taken up by damaged cardiac tissue.

The complexing agents useful in this invention, which are derivatives of 3(4),8(9)-bis(aminomethyl)-tricyclo[5.2.1.0$^{2,6}$]decane, also called dicyclopentadienebis(methylamine), are disclosed as new compounds in copending application entitled "New Metal Ion Control Agents Based on Dicyclopentadiene Derivatives," Ser. No. 486,122, filed Apr. 18, 1983.

PREPARATION OF THE COMPLEX

Deionized water (100 g) and 49.0 g (0.25 mole) of 3(4),8(9)-bis(aminomethyl)-tricyclo[5.2.1.0$^{2,6}$]-decane were weighed into a 500-ml round-bottom reaction flask equipped with a water-cooled reflux condenser, mechanical stirrer, thermometer, with a temperature controller, and an addition funnel. Approximately 120 g of concentrated HCl solution and 98.7 g (1.20 mole) of phosphorous acid were added to the aqueous amine solution and the reaction mixture heated to reflux and maintained for one hour. Aqueous 37% formaldehyde solution (85.1 g, 1.05 mole) was placed in the addition funnel and added to the reactor over a two-hour period. The reaction mixture was heated at reflux for an additional two hours and then cooled. Ethanol was added to the solution until a precipitate formed. The white solid was filtered and dried.

Ten milligrams of the above solid was dissolved in one ml of 0.9% NaCl solution and bubbled with $N_2$. The pH was adjusted to 3 using dilute NaOH and HCl and 0.1 ml of freshly eluted NaTcO$_4$ solution from a generator was added. To this solution, 100 ml of freshly prepared stannous tartrate (SnC$_4$H$_4$O$_6$) was added. Paper chromatography using saline and acetone as eluents showed less than 5% of the activity as TcO$_4^-$ or reduced uncomplexed Tc.

The following examples show the use of the complex and the results obtained.

EXAMPLE 1

Heart damage was induced in laboratory rats (215-285 g body weight) by injecting subcutaneously with isoproterenol hydrochloride (15 mg/ml isotonic saline) solutions. The dosage used was proportional to the weight of the rats (30 mg isoproterenol hydrochloride/kilogram of body weight).

After five hours, the animals were injected with 50 μl (~1 mCi) of the above radioactive solution via the tail vein. The animals were killed by cervical dislocation 60 minutes after the injection of the technetium complex. The heart was excised, cut open, and blotted. Heart tissue was then washed with isotonic saline solution and weighed. Other organs were also dissected and weighed. The amount of radiation in each tissue was quantitatively determined using a NaI scintillation counter. Fifty μl standards of the complex solution were also counted. Commercial kits of methylenediphosphonate and pyrophosphate were also used in the same manner for comparison. Table I shows the levels found in the blood, liver, and muscle for several agents. The levels are expressed as a percent of the original dose of radioactivity which was taken up by the tissue or fluid (blood).

TABLE I

| | % Dose/g of Tissue (Fluid) | | |
|---|---|---|---|
| | Blood | Liver | Muscle |
| Pyrophosphate | 0.182 | 0.131 | 0.026 |
| Methylenediphosphonate | 0.051 | 0.060 | 0.018 |
| Complex of Invention | 0.062 | 0.061 | 0.017 |

Control animals (animals not injected with isoproterenol) were also injected with several $^{99m}$Tc complexes. The ratio of activity in damaged cardiac tissue compared to normal cardiac tissue is given in Table II.

TABLE II

| % Dose/gram in Damaged Heart/% Dose/gram in Normal Heart | | |
|---|---|---|
| Methylenediphosphonate | Pyrophosphate | Complex of Invention |
| 20.5 | 21.4 | 22.7 |

EXAMPLE 2

Heart damage was induced in laboratory rats and they were then injected with the radioactive complex of Example 1 as above. After one hour, the rats were anesthetized and scintillation scans of the chest area taken using a gamma camera. The scan using the above radioactive complex showed clearly the outline of the heart with relatively little interference with the ribs or the sternum.

We claim:

1. In a process in which cardiac infarcts are imaged with a complex of a radionuclide the improvement which comprises employing as the complexing agent a compound having the formula

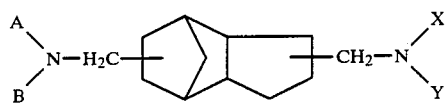

wherein substituents A, B, X and Y are each independently selected from radicals including hydrogen, hydroxyalkyl (wherein the alkyl group contains 2-6 carbon atoms), methylenephosphonic, methylene-, ethylene-, and propylenesulfonic, carboxylic acid radicals (having 2-4 carbon atoms) and the alkali or alkaline earth metal, ammonia and amine salts thereof and wherein at least one A, B, X and Y is methylenephosphonic acid or a salt thereof.

2. The process or claim 1 wherein A, B, X and Y are each a methylenephosphonic acid or a salt thereof.

3. The process of claim 1 wherein the radionuclide is technetium-99m.

4. The process of claim 2 wherein the radionuclide is technetium-99m.

* * * * *